United States Patent
Remaut et al.

(10) Patent No.: US 11,540,982 B2
(45) Date of Patent: Jan. 3, 2023

(54) DEMAKE-UP MICELLAR MILK

(71) Applicant: L'OREAL, Paris (FR)

(72) Inventors: Geoffroy Remaut, Chevilly la Rue (FR); Anne-Marie Jammes-Saint Martin, Chevilly la Rue (FR)

(73) Assignee: L'OREAL, Paris (FR)

( * ) Notice: Subject to any disclaimer, the term of this patent is extended or adjusted under 35 U.S.C. 154(b) by 237 days.

(21) Appl. No.: 16/764,037

(22) PCT Filed: Nov. 16, 2018

(86) PCT No.: PCT/EP2018/081632
§ 371 (c)(1),
(2) Date: May 14, 2020

(87) PCT Pub. No.: WO2019/097022
PCT Pub. Date: May 23, 2019

(65) Prior Publication Data
US 2020/0281825 A1  Sep. 10, 2020

(30) Foreign Application Priority Data

Nov. 16, 2017  (FR) ...................................... 1760800

(51) Int. Cl.
*A61K 8/06* (2006.01)
*A61Q 1/14* (2006.01)
*A61K 8/81* (2006.01)
*A61K 8/73* (2006.01)

(52) U.S. Cl.
CPC ................ *A61K 8/062* (2013.01); *A61K 8/73* (2013.01); *A61K 8/8147* (2013.01); *A61K 8/8152* (2013.01); *A61Q 1/14* (2013.01)

(58) Field of Classification Search
CPC ........ A61K 8/73; A61K 8/062; A61K 8/8152; A61K 8/8147; A61K 8/731; A61Q 1/14
See application file for complete search history.

(56) References Cited

U.S. PATENT DOCUMENTS

| 8,048,920 B2* | 11/2011 | Joerger | A23B 7/154 |
| | | | 514/552 |
| 2015/0342857 A1* | 12/2015 | Degeorge | A61Q 5/04 |
| | | | 424/70.16 |
| 2016/0175233 A1 | 6/2016 | Benn | |
| 2018/0353405 A1* | 12/2018 | Flohr | A61Q 5/10 |

FOREIGN PATENT DOCUMENTS

| CN | 104921960 A | 9/2015 |
| CN | 105848626 A | 8/2016 |
| CN | 106457002 A | 2/2017 |
| CN | 106535869 A | 3/2017 |
| EP | 1302190 A1 | 4/2003 |
| EP | 3 021 830 A1 | 5/2016 |
| FR | 3 022 774 A1 | 6/2014 |
| WO | WO 2012/059348 | 5/2012 |
| WO | WO 2013/076238 A1 | 5/2013 |
| WO | WO 2014/210466 A1 | 12/2014 |
| WO | WO 2015/099198 A1 | 7/2015 |

OTHER PUBLICATIONS

Database GNPD [Online] Mintel; "Water-Infused Brightening Gel Mask", Aug. 2017.
Database GNPD [Online] Mintel: "Heel Chemistry ", Deciem, The Chemistry Brand, Mar. 2017.
Modern Cosmetics Science and Technology, Section 3.8.4 Acrylate/ C10-C30 alkyl Acrylate Cross Copolymer Emulsifies, 2016.

* cited by examiner

*Primary Examiner* — Jianfeng Song
(74) *Attorney, Agent, or Firm* — Polsinelli PC

(57) ABSTRACT

This invention relates to a composition, preferably a demake-up cosmetic composition, comprising: an oily phase dispersed in an aqueous phase, at least one homopolymer of non-superabsorbent acrylic acid that is at least partially neutralized, at least one cross-linked copolymer of (meth) acrylic acid and of C1-C6 alkyl acrylate, at least one polysaccharide gelling agent comprising at least one glucose monomer, and said composition having a pH greater than or equal to 5.5. It also relates to the use of such a composition for the demake-up of keratin materials.

18 Claims, No Drawings

DEMAKE-UP MICELLAR MILK

CROSS REFERENCE TO RELATED APPLICATIONS

This application is a National Phase filing under 35 U.S.C. § 371 of PCT/EP2018/081632 filed on 16 Nov. 2018; which application in turn claims priority to Application No. 1760800 filed in France on 16 Nov. 2017. The entire contents of each application are hereby incorporated by reference.

This invention relates to a composition, preferably a cosmetic composition, in particular demake-up, in the form of an oil-in-water (O/W) emulsion and comprising at least one non-superabsorbent acrylic acid homopolymer that is at least partially neutralized, at least one cross-linked copolymer of (meth)acrylic acid and of C1-C6 alkyl acrylate, at least one polysaccharide gelling agent comprising at least one glucose monomer, and having a pH greater than or equal to 5.5; and the use of such a composition; as well as a method of makeup removal and/or cleaning using such a composition.

Skin makeup removal is very important for the care of keratin materials (i.e. skin and keratinous fibers such as the eyelashes). It must be as effective as possible because the fatty residues such as excess sebum, the remainder of cosmetic products used daily and makeup products accumulate in particular in the skin folds and on th surface of the skin, and can obstruct the pores of the skin and thus cause the appearance of pimples. However, today, consumers demand that make-up products last increasingly longer: waterproof mascaras, long-lasting foundations and without transfer, lipsticks that last all day.

Moreover, the demake-up formulas that are currently available often have a thick texture, and leave a residual film on the skin that is not very pleasant.

Furthermore, most demake-up compositions available are two-phase compositions, i.e. comprised of two separate phases, in particular an aqueous phase and an oily phase, that require prior shaking before application. Such formulations allow for a good make-up removal, but leave a finish on the skin that is often oily.

Finally, there are also micellar waters, which a single-phase fluid compositions that give freshness to the application. Such compositions however have little effect on long-lasting make-up, and in general have no additional benefit.

There is therefore a need for effective demake-up compositions, that have a fluid texture, and which do not require any shaking before application, while remaining stable. Such compositions must also provide the application with a benefit.

The Applicant surprisingly discovered that a O/W emulsion with a pH greater than or equal to 5.5 and comprising a non-superabsorbent acrylic acid homopolymer that is at least partially neutralized, a cross-linked copolymer of (meth)acrylic acid and of C1-C6 alkyl acrylate, and a specific polysaccharide gelling agent, has a very fluid texture, of the dietary milk type. This composition is stable; it is easy and very pleasant to apply. It is opaque, and does not require any shaking prior to application. It makes it possible to effectively demake-up cosmetic compositions of coating keratin materials, preferably from the skin or keratin fibers. Furthermore, it provides a benefit at application, because it makes it possible to moisturize the keratin materials, preferably the skin.

Therefore the purpose of this invention is a composition, preferably a demake-up cosmetic composition, comprising:
- an oily phase dispersed in an aqueous phase,
- at least one homopolymer of non-superabsorbent acrylic acid that is at least partially neutralized,
- at least one cross-linked copolymer of (meth)acrylic acid and of C1-06 alkyl acrylate,
- at least one polysaccharide gelling agent comprising at least one glucose monomer, and said composition having a pH greater than or equal to 5.5.

The composition according to the invention is an O/W emulsion. The composition according to the invention is preferably stable. The term "stable" means that the composition according to the invention remains homogeneous over time, for a period of at least 2 months at 45° C., and does not have any coalescence phenomenon.

This invention also has for purpose a method of makeup removal and/or cleaning of keratin materials, preferably the skin and/or keratin fibers such as eyelashes, comprising the application on the keratin materials of a composition according to the invention.

Viscosity

Compositions according to the invention are fluid.

Compositions according to the invention preferably have a viscosity less than 250 Cps, preferably less than 170 Cps.

The measurement protocol of the viscosity is as follows:

The viscosity is measured is generally taken at 20° C., using a RHEOMAT RM 180 viscometer equipped with a moving body no 4, the measurement being made after 10 minutes of rotation of the moving body (time after which stabilization of the viscosity and rotational speed of the moving body is observed), at a shear rate of 200 $s^{-1}$.

The constituents of the composition according to the invention are now described in more detail.

At least Partially Neutralized Non-Superabsorbent Acrylic Homopolymers

The composition according to the invention comprises at least one non-superabsorbent acrylic acid homopolymer that is at least partially neutralized.

All non-superabsorbent acrylic acid homopolymers can be used with this invention, provided that they are hydrophilic and are used in at least partially neutralized form.

A "superabsorbent polymer" means a polymer that in its dry state, is capable of spontaneously absorbing at least 20 times its own weight of aqueous fluid, and particularly water and especially distilled water. Such superabsorbent polymers are described in the book "Absorbent polymer technology, Studies in polymer science 8" by L. BRAN NON-PAPPAS and R. HARLAND, published by Elsevier, 1990.

In the framework of the invention, a non-superabsorbent polymer is a polymer that does not comply with the definition given above for superabsorbent polymers.

For the purposes of this invention, "hydrophilic polymer" means a polymer that is soluble or dispersible in water at 25° C. Non-superabsorbent acrylic homopolymers suitable for this invention may be present in the composition in particulate or non-particulate form.

When they are present in particulate form, their average size in the hydrated state is preferably less than or equal to 10 μm, and even more preferably less than or equal to 5 μm. Their average size in the dry or non-hydrated state is preferably less than or equal to 2 μm, and more preferably less than or equal to 1 μm.

Preferable, the at least partially neutralized non-superabsorbent acrylic acid homopolymer according to the invention is present in non-particulate form.

Preferably, a non-superabsorbent acrylic acid homopolymer that is at least partially neutralized is used. The homopolymer used in this invention is chosen particularly among sodium polyacrylates and potassium polyacrylates. Sodium polyacrylate is preferably used.

Non-superabsorbent acrylic homopolymers that are already neutralized before their use include for example:
  sodium polyacrylates such as those marketed under the trade name Cosmedia SP® containing 90% of dry material and 10% of water, or Cosmedia SPL® in inverse emulsion containing about 60% of dry active material, an oil (hydrogenated polydecene) and a surfactant (PPG-5 Laureth-5), both sold by the Cognis company;
  partially neutralized sodium polyacrylates, particularly in the form of an inverse emulsion comprising at least one polar oil, for example that sold under the trade name Luvigel® EM by the BASF company; and
  mixtures thereof.

A non-superabsorbent acrylic acid homopolymer that is not previously neutralized can also be used, and in this case it is neutralized before use by any appropriate means and particularly the addition of soda. This results in sodium polyacrylates. Potassium polyacrylates are also suitable for this invention.

On the other hand, for some of them, neutralization is inherent to the raw material. This is the case particularly for Luvigel® EM and products called Cosmedia® SP and SPL that are already partially neutralized. The neutralization step, for example by sodium or potassium counter ions, is important to confer gelling properties on acid polymers, and therefore for stabilization of the composition. Said acrylic polymers are converted into corresponding acrylate polymers during this neutralization step. Acrylic monomers of the acrylic polymer according to the invention can be neutralized from 5% to 100%, and particularly from 5% to 80%. Thus, preferably, an acrylic acid homopolymer neutralized to a content of 5% to 100% is used, and particularly from 5% to 80%.

According to one particular embodiment, the acrylic acid homopolymer can be found in the form of a water-in-oil emulsion, called an inverse emulsion. For example, this inverse emulsion can be obtained by polymerization in inverse emulsion.

According to one particular embodiment of the invention, the homopolymer used is a partially neutralized sodium polyacrylate in the form of an inverse emulsion comprising at least one polar oil.

Fatty acid esters can be mentioned as suitable oils. Examples of these fatty acid esters include fatty acid isopropylic esters such as isopropyl palmitate or isopropyl myristate or fatty acid polyglycerides, particularly mixes of fatty acids containing at least 50% of capric and/or caprylic acids. Such water-in-oil emulsions are described in document U.S. Pat. No. 6,197,283. According to this embodiment, the oily phase may be composed of one or several fatty acid esters, one or several fatty acid polyglycerides based on a mixture of polyglycerides, containing diglycerides and triglycerides, with mixes of fatty acids that contain caprylic acid and/or capric acid, preferably with a content of at least 50% by weight relative to the total weight of fatty acids.

According to one embodiment of the invention, the oil content of the inverse emulsion is between 15% and 70% by weight, particularly between 20% and 35% by weight relative to the total weight of the inverse emulsion. In this respect, Luvigel® EM in particular can be mentioned, for which the oily phase comprises 26% of oil phase composed of C8-10 triglycerides, namely for which the fatty acids are a mixture of capric acid and caprylic acid.

Furthermore, the water-in-oil emulsion can contain 0.25% to 7% by weight, preferably 0.5% to 5% by weight, of a surfactant.

The at least partially neutralized acrylic homopolymer can be present in the inverse emulsion with a total content ranging from 20% to 70% by weight, particularly from 20% to 65% by weight, and for example from 20% to 62% by weight in relation to the total weight of the inverse emulsion.

In particular, according to one embodiment, the acrylic homopolymer may be present in the inverse emulsion with a content varying from 20% to 30% by weight relative to the total weight of the inverse emulsion.

According to yet another embodiment, the acrylic homopolymer may be present in the inverse emulsion with a content varying from 50% to 62% by weight relative to the total weight of the composition.

The acrylic homopolymer(s) can be present in the composition according to the invention with a total content of active material ranging from 0.01% to 0.6% by weight, and preferably from 0.1% to 0.45% by weight, and more preferably from 0.2% to 0.35% by weight in relation to the total weight of the composition.

Cross-Linked Copolymer of (Meth)Acrylic Acid and of C1-C6 Alkyl Acrylate

The composition according to the invention comprises at least one cross-linked copolymer of (meth)acrylic acid and of C1-C6 alkyl acrylate.

The monomer of (meth)acrylic acid is present preferably in quantities ranging from 20 to 80% by weight, and more particularly from 25 to 70% by weight, even more particularly from 35 to 60% by weight with respect to the total weight of the copolymer.

The monomer of C1-C6 alkyl acrylate is present preferably in quantities ranging from 15 to 80% by weight and more particularly from 25 to 75% by weight and even more particularly from 40 to 65% by weight with respect to the total weight of the copolymer. Among these monomers, mention can be made of methyl acrylate, ethyl acrylate, n-butyl acrylate, 2-hydroxyethyl acrylate, styrene, acrylamide, N,N-dimethylacrylamide, tertio-butylacrylamide, methyl methacrylate, ethyl methacrylate, n-butyl methacrylate, 2-hydroxyethyl methacrylate.

The copolymer is typically partially or entirely cross-linked by at least one conventional cross-linking agent. The cross-linking agents are in particular polyunsaturated compounds. These compounds are in particular polyalkenylethers of sucrose or of polyols, diallylphthalates, divinylbenzene, allyl (meth)acrylate, ethyleneglycol di(meth)acrylate, methylene bis-acrylamide, trimethylol propane tri(meth)acrylate, diallyl itaconate, diallyl fumarate, diallyl maleate, zinc (meth)acrylate, derivatives of castor oil or of polyols manufactured from unsaturated carboxylic acids.

As a cross-linking agent, unsaturated monomer compounds and which comprise a reactive group able to react with an unsaturation in order to form a cross-linked copolymer can also be used.

The content of cross-linking agent varies in general from 0.01 to 5% by weight and preferably from 0.03 to 3% by weight and even more particularly from 0.05 to 1% by weight with respect to the total weight of the copolymer.

The preferred copolymer according to the invention is chosen from a cross-linked copolymer of methacrylic acid and of C1-C6 alkyl acrylate, a cross-linked copolymer of acrylic acid and C1-C6 alkyl acrylate and more particularly a cross-linked copolymer of methacrylic acid and ethyl acrylate.

According to a particularly preferred embodiment, the copolymer of the invention can have in particular the form of a dispersion in water. The average size in number of particles of copolymer in the dispersion is generally between 10 and 500 nm and preferably between 20 and 200 nm and more preferably from 50 to 150 nm.

Among the cross-linked copolymers of (meth)acrylic acid and of C1-C6 alkyl acrylate, mention can be made of the product sold under the trade name VISCOATEX 538C by COATEX which is a C1-C4 cross-linked copolymer of (meth)acrylic and ethyl acrylate in an aqueous dispersion at 38% of active material, or the product sold under the trade name ACULYN 33 by ROHM & HAAS which is a cross-linked copolymer of acrylic acid and ethyl acrylate in aqueous dispersion at 28% of active material. Mention can be made more particularly of cross-linked methacrylic acid/ethyl acrylate copolymer in the form of an aqueous dispersion at 30% manufactured and sold under the name CARBOPOL AQUA SF-1 by NOVEON.

The concentration in cross-linked copolymer (i.e. in active material) generally ranged from 0.01 to 0.6% by weight in relation to the total weight of the composition, and preferably from 0.1 á 0.5% by weight, and even more particularly from 0.2 to 0.4% by weight.

Gelling Agent

The composition according to the invention comprises at least one polysaccharide gelling agent comprising at least one glucose monomer.

As polysaccharide gelling agents, mention can be made of homo- and heteropolysaccharides comprising at least one glucose monomer, and in particular xanthan gum, amylopectin or cellulose and derivatives thereof.

Among the cellulose derivatives, mention can be made in particular of carboxymethyl cellulose, in particular PURIFIED SODIUM CARBOXYMETHYL CELLULOSE DE sold by Ashland under the trade name Aqua Sorb A 500.

Preferably, the composition according to the invention comprises xanthan gum or cellulose or derivatives thereof.

The polysaccharide gelling agent or agents comprising at least one glucose monomer can be present in the composition according to the invention with a total content of active material ranging for example from 0.01 to 0.5% by weight, preferably from 0.05 to 0.3% by weight, preferably ranging from 0.07 to 0.2% by weight in relation to the total weight of the composition.

pH of the Composition

The composition according to the invention has a pH greater than or equal to 5.5 at 25° C., preferably greater than or equal to 5.9, preferably greater than or equal to 6.0. Advantageously, the pH of the composition is between 5.9 and 7, preferably between 6.0 and 6.5.

According to an embodiment, the cosmetic composition according to the invention can comprise an acid and a base.

According to an alternative, the composition according to the invention may comprise at least one base.

The base may be chosen from mineral bases such as for example alkaline metal hydroxides, sodium hydroxide, potassium hydroxide, ammonium hydroxides, ammonia, organic bases such as for example monoethanolamine, diethanolamine, triethanolamine, triisopropylamine, tri[(2-hydroxy) 1-propyl)] amine, N,N-dimethyl ethanolamine, 2-amino 2-methyl 1-propanol, 2-amino 2-methyl 1,3-propanediol, triethylamine, dimethylaminopropylamine and amphoteric bases (i.e. bases having both anionic and cationic functional groups) such as primary, secondary, tertiary or cyclic organic amines, amino acids. By way of example of amphoteric bases, mention may be made of glycine, lysine, arginine, taurine, histidine, alanine, valine, cysteine, trihydroxymrehylaminomethane (TRISTA), triethanolamine and any of the mixtures thereof.

According to one particular embodiment, the base of the composition is chosen from sodium hydroxide, potassium hydroxide, ammonium hydroxides, ammonia, monoethanolamine, diethanolamine, triethanolamine, tromethamine and any of the mixtures thereof. According to one particular embodiment, the base of the composition is chosen from among sodium hydroxide, triethanolamine, and mixtures thereof.

According to one particular embodiment, the base of the composition according to the invention is present at a mass concentration less than 0.5%, preferably less than 0.25% by mass with respect to the total mass of the composition.

According to one alternative embodiment, the composition according to the invention may comprise at least one acid.

The acid may be chosen from inorganic acids such as hydrochloric acid, sulfuric acid, nitric acid, organic acids such as acetic acid, lactic acid, glycolic acid, mandelic acid, citric acid, ascorbic acid and any of the mixtures thereof.

The acid may be chosen from among organic acids such as benzoic acid, anisic acid, salicylic acid and any mixture thereof.

According to one particular embodiment, the acid of the composition according to the invention is present at a mass concentration less than 0.5%, preferably less than 0.25% by mass with respect to the total mass of the composition.

Aqueous Phase

The composition according to the invention comprises a physiologically acceptable aqueous phase. "Physiologically acceptable" means a medium compatible with keratin materials.

The composition according to the invention preferably comprises an aqueous phase comprising water and possibly one or several organic solvents soluble in water at 25° C. These solvents can advantageously be chosen for example from among linear or branched alkanols, in C2-C4, such as ethanol and isopropanol, propanol, butanol; polyols particularly with 2 to 20 carbon atoms, preferably 2 to 6 carbon atoms such as glycerol, diglycerol, propyleneglycol, glycol isoprene, dipropyleneglycol, butylene glycol, hexylene glycol, 1,3-propanediol, pentylene glycol, polyethyleneglycols with 2 to 200 ethylene oxide motifs, and mixtures thereof.

The composition generally comprises from 50% to 98% by weight of water with respect to the total weight of the composition, preferably from 60 to 95% by weight, preferably from 80% to 90% by weight.

The quantity of organic solvents can range for example from 0.01% to 15% by weight, preferably from 0.5% to 13% by weight, better from 1% to 10% by weight, better from 3% to 10% by weight relative to the total weight of the composition.

The composition according to the invention comprises a fatty phase dispersed in aqueous phase: this is an oil-in-water emulsion.

Oily Phase

The composition according to the invention comprises a dispersed oily phase. This oily phase is also called fatty phase.

Preferably, the oily phase of the composition according to the invention represents a percentage ranging from 0.1% by 10%, preferably ranging from 0.5% to 5% and even more preferably ranging from 1% to 3% with respect to the total weight of the composition.

In particular, the oily phase of the composition according to the invention can comprise one or several liquid non-fatty oil or fatty body at ambient temperature (25° C.) and atmospheric pressure (760 mm of Hg). It can also comprise one or several solid non-aqueous fatty bodies at ambient temperature (25° C.) and atmospheric pressure (760 mm of Hg), such as waxes.

The oil can be chosen from volatile oils and/or non-volatile oils, and mixtures thereof.

The term "volatile oil" is intended to mean any oil capable of evaporating on contact with keratin fibers, in less than one hour, at ambient temperature and at atmospheric pressure. The volatile oil or oils according to the invention are volatile cosmetic oils, which are liquid at ambient temperature, having a vapor pressure different to zero, at ambient temperature and atmospheric pressure, particularly ranging from 0.13 Pa to 40,000 Pa ($10^{-3}$ at 300 mm Hg), particularly ranging from 1.3 Pa to 13,000 Pa (0.01 to 100 mm Hg), and more specifically ranging from 1.3 Pa to 1300 Pa (0.01 at 10 mm Hg). The term "non-volatile oil" denotes an oil remaining on skin or keratin fiber at ambient temperature and atmospheric pressure and particularly having a vapor pressure less than $10^{-3}$ mm Hg (0.13 Pa) at ambient temperature (25° C.).

These oils may be hydrocarbon oils, silicone oils, fluorinated oils or mixtures thereof.

A "hydrocarbon oil" is an oil containing principally hydrogen and carbon atoms and possible oxygen, nitrogen, sulfur and phosphorus atoms. The volatile hydrocarbon oils can be chosen from hydrocarbon oils having 8 to 16 carbon atoms, and particularly branched C8-C16 alkanes such as petroleum-based C8-C16 isoalkanes (also referred to as isoparaffins) such as isododecane (also referred to as 2,2,4,4,6-pentamethylheptane), isodecane, isohexadecane, and for example oils sold under the trade names Isopars or Permetyls, branched C8-C16 esters, isohexyl neopentanoate, and mixtures thereof. Further volatile hydrocarbon oils such as petroleum distillates, particularly those sold under the name Shell Solt by SHELL, may also be used.

Other volatile oils that can be used are volatile silicones, such as for example volatile linear or cyclic silicone oils, particularly those having a viscosity ≤8 centistokes (8 10–6 m2/s), and in particular having 2 to 7 silicon atoms, these silicones optionally comprising alkyl or alkoxy groups having 1 to 10 carbon atoms. Mention may be made, as a volatile silicone oil suitable for use in the invention, in particular, of octamethyl cyclotetrasiloxane, decamethyl cyclopentasiloxane, dodecamethyl cyclohexasiloxane, heptamethyl hexyltrisiloxane, heptamethyloctyl trisiloxane, hexamethyl disiloxane, octamethyl trisiloxane, decamethyl tetrasiloxane, dodecamethyl pentasiloxane, and mixtures thereof.

Mention may also be made of volatile alkyl trisiloxane oils with general formula (I):

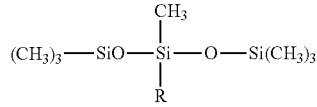

(I)

In which R represents an alkyl group comprising 2 to 4 carbon atoms and in which one or several hydrogen atoms can be substituted by a fluorine or chlorine atom. Among oils with general formula (I), mention may be made of:
3-butyl 1,1,1,3,5,5,5-heptamethyl trisiloxane,
3-propyl 1,1,1,3,5,5,5-heptamethyl trisiloxane, and
3-ethyl 1,1,1,3,5,5,5-heptamethyl trisiloxane,
corresponding to the oils having formula (I) for which R is respectively a butyl group, a propyl group or an ethyl group.

The composition can also comprise at least one non-volatile oil, and in particular chosen from non-volatile hydrocarbon and/or silicone and/or fluorinated oils.

As a non-volatile hydrocarbon oil, mention may be made of:
hydrocarbon oils of plant origin such as triesters of fatty acids and glycerol for which the fatty acids can have chain lengths ranging from C4 to C24, with the latter able to be linear or branched, saturated or unsaturated; these oils are in particular wheat germ, rice bran, sunflower, grape seed, sesame, corn, apricot, castor, shea, avocado, olive, soybean oils, sweet almond, palm, rapeseed, cotton, hazelnut, macadamia, jojoba, alfalfa, poppy seed, pumpkin, sesame, squash, rapeseed, blackcurrant, evening primrose, millet, barley, quinoa, rye, safflower, candlenut, passiflora, musk rose oil; or caprylic/capric acid triglycerides such as those sold by Stearineries Dubois or those sold under the trade names Miglyol 810, 812 and 818 by Dynamit Nobel;
linear or branched hydrocarbons of mineral or synthetic origin, such as liquid paraffins and derivatives thereof, polydecenes, polybutenes, hydrogenated polyisobutene such as Parleam, squalane;
synthetic ethers having from 10 to 40 carbon atoms;
synthetic esters such as the oils having the formula R1COOR2 wherein R1 represents the residue of a linear or branched fatty acid comprising 1 to 40 carbon atoms and R2 represents a hydrocarbon chain, particularly branched containing 1 to 40 carbon atoms where R1+R2≥10, such as for example Purcellin oil (cetostearyl octanoate), isopropyl myristate, isopropyl palmitate, C12 to C15 alcohol benzoate, hexyl laurate, diisopropyl adipate, isononyl isononanoate, 2-ethylhexyl palmitate, isostearate of isostearate, alcohol or polyalcohol octanoates, decanoates or ricinoleates such as propylene glycol dioctanoate; hydroxylated esters, such as isostearyl lactate, diisostearyl malate; and pentaerythritol esters;
fatty alcohols that are liquid at ambient temperature, with a branched and/or unsaturated carbon chain having 12 to 26 carbon atoms, such as octyldodecanol, isostearyl alcohol, oleic alcohol, 2-hexyldecanol, 2-butyloctanol, 2-undecylpentadecanol;
higher fatty acids, such as oleic acid, linoleic acid, linolenic acid;
carbonates;
acetates;
citrates;
and mixtures thereof.

The non-volatile silicone oils that can be used in the composition in accordance with the invention can be non-volatile polydimethylsiloxanes (PDMS), polydimethylsiloxanes comprising alkyl or alkoxy groups which are pendant or at the end of the silicone chain, groups each having 2 to 24 carbon atoms; phenylated silicones, such as phenyl trimethicones, phenyl dimethicones, phenyltrimethylsiloxydiphenylsiloxanes, diphenyl dimethicones, diphenylmethyldiphenyl-trisiloxanes or (2-phenylethyl)trimethylsiloxysilicates.

The fluorinated oils that can be used in the invention are in particular fluorosilicone oils, fluorinated polyethers, fluorinated silicones, as described in document EP-A-847752.

Preferably, the composition according to the invention comprises at least one non-volatile hydrocarbon oil. Preferably, the non-volatile hydrocarbon oil is chosen from hydrocarbon oils of plant origin and the oils having the formula R1COOR2 mentioned hereinabove, wherein R1 represents the residue of a linear or branched fatty acid comprising 1 to 40 carbon atoms and R2 represents a hydrocarbon chain, particularly branched containing 1 to 40 carbon atoms where R1+R2≥10.

The composition according to the invention can comprise at least one wax. Preferably, if a wax is present, it is present in a quantity less than 5% by weight in relation to the total weight of the composition.

The term "wax" refers to a lipophilic compound, which is solid at ambient temperature (25° C.), deformable or not, having a reversible solid/liquid change of state and a melting point greater than or equal to 40° C. that can range up to 120° C.

For the purposes of the invention, the melting temperature is the temperature of the most endothermic peak observed in thermal analysis (DSC), such as described in ISO standard 11357-3: 1999. The melting point of the wax can be measured using a differential scanning calorimeter (DSC), for example the calorimeter sold under the trade name "MDSC 2920" by TA Instruments. The measurement protocol is as follows:

A 5 mg sample of wax placed in a crucible is subjected to a first temperature rise from −20° C. to 100° C., at a heating rate of 10° C./minute, and is then cooled from 100° C. to −20° C. at a cooling rate of 10° C./minute and finally subjected to a second temperature rise from −20° C. to 100° C. at a heating rate of 5° C./minute. During the second temperature rise, the variation in the difference in power absorbed by the empty crucible and by the crucible containing the wax sample as a function of temperature is measured. The melting point of the compound is the value of the temperature equivalent to the top point of the peak of the curve representing the variation in the difference in power absorbed as a function of temperature.

Hydrocarbon waxes such as beeswax, lanolin wax; rice wax, Carnauba wax, Candellila wax, Ouricury wax, Japan wax, Berry wax, shellac wax and sumac wax; montan wax can be in particular used as wax.

Mention may also be made of waxes obtained by means of the catalytic hydrogenation of animal or plant oils having C8-C32 linear or branched fat chains. Of these, particular mention may be made of hydrogenated jojoba oil, hydrogenated palm oil, hydrogenated sunflower oil, hydrogenated castor oil, hydrogenated coconut oil, hydrogenated lanolin oil, di-(trimethylol-1,1,1propane) tetrastearate sold under the name "HEST 2T-4S" by HETERENE, di-(trimethylol-1,1,1propane) tetrabehenate sold under the name HEST 2T-4B by HETERENE.

The wax used can also be obtained by hydrogenating esterified olive oil with stearyl alcohol sold under the name "PHYTOWAX Olive 18 L 57" or waxes obtained by hydrogenating esterified castor oil with cetyl alcohol sold under the name "PHYTOWAX ricin 16L64 and 22L73", by SOPHIM. Such waxes are described in the application FR-A-2792190.

A silicone wax, in particular sticky, such as a C20-C40 alkyl (hydroxystearyloxy)stearate (the alkyl group comprising 20 to 40 carbon atoms), alone or in a mixture, may be used, in particular a C20-C40 12-alkyl-(12'-hydroxystearyloxy)stearate having the formula (I):

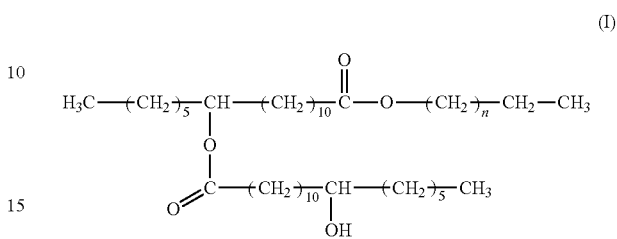

wherein n is an integer ranging from 18 to 38, or a mixture of compounds having the formula (1). Such a sticky wax is particularly sold under the names "KESTER WAX K 82 P" and "KESTER WAX K 80 P" by KOSTER KEUNEN.

Mention can finally be made of microcrystalline waxes, paraffins and ozokerite; polyethylene waxes, waxes obtained by means of Fisher-Tropsch synthesis and waxy copolymers and the esters thereof; silicone waxes and fluorinated waxes.

Surfactants

The composition according to the invention can also comprise at least one surfactant.

This surfactant can be anionic, non-ionic, amphoteric, zwitterionic or cationic. It is generally introduced in the aqueous phase.

It can be hydrocarbon or silico, and can have at 25° C. a HLB balance (Hydrophilic-Lipophilic Balance) in terms of GRIFFIN, preferably greater than or equal to 8.

The HLB value as per GRIFFIN is defined in J. Soc. Cosm. Chem. 1954 (volume 5), pages 249-256. Reference may be made to the document "Encyclopedia of Chemical Technology, KIRK-OTHMER", volume 22, p. 333-432, 3rd edition, 1979, WILEY, for the definition of the properties and emulsifying functions of surfactant agents, in particular p. 347-377 of this reference.

Preferably, the surfactant according to the invention is chosen from:
b) anionic surfactants such as:
polyoxyethylenated fatty acid salts and particularly those derived from alkaline salts, and mixtures thereof;
phosphoric esters and their salts such as "DEA oleth-10 phosphate" (Crodafos N 10N from CRODA) or monopotassium monocetyl phosphate (Amphisol K from Givaudan);
sulfosuccinates such as "Disodium PEG-5 citrate lauryl sulfosuccinate" and "Disodium ricinoleamido MEA sulfosuccinate";
alkylethersulfates such as sodium lauryl ether sulfate; isethionates;
acylglutamates such as "Disodium hydrogenated tallow glutamate" (AMISOFT HS-21 R® marketed by AJINOMOTO) and sodium stearoyl glutamate (AMISOFT HS-11 PF® marketed by AJINOMOTO) and mixtures thereof;
derivatives of soybeans such as potassium soyate;
citrates, such as Glyceryl stearate citrate (Axol C 62 Pellets from Degussa);
derivatives of proline, such as Sodium palmitoyl proline (Sepicalm VG from Seppic), or the Mixture of Sodium palmitoyl sarcosinate, Magnesium palmitoyl glutamate, palmitic acid and Palmitoyl proline (Sepifeel One from Seppic);

lactylates, such as Sodium stearoyl lactylate (Akoline SL from Karlshamns AB);

sarcosinates, such as sodium palmitoyl sarcosinate (Nikko) sarcosinate PN) or the mixture of Stearoyl sarcosine and Myristoyl sarcosine 75/25 (Crodasin SM from Croda);

sulfonates, such as Sodium C14-17 alkyl sec sulfonate (Hostapur SAS 60 from Clariant);

glycinates, such as sodium cocoyl glycinate (Amilite GCS-12 from Ajinomoto).

C16-C30 fatty acid salts in particular those derived from amines, such as triethanolamine stearate and/or amino-2-methyl-2-propane di-ol-1,3 stearate;

b) amphoteric or zwitterionic surfactants, such as N-acyl-aminoacids such as N-alkyl-aminoacetates (such as trimethylglycine), disodium cocoamphodiacetate, amine oxides such as stearamine oxide or even silicone surfactants such as dimethicone copolyol phosphates such as the one sold under the trade name PECOSIL PS 100® by PHOENIX CHEMICAL;

c) non-ionic surfactants with a HLB greater than or equal to 8 at 25° C., such as:

esters and ethers of oses such as the mixture of cetyl-stearyl glucoside and cetyl and stearyl alcohols such as Montanov 68 from Seppic;

oxyethylene and/or oxypropylene ethers (that may comprise from 1 to 150 oxyethylene and/or oxypropylene groups) of glycerol;

oxyethylene and/or oxypropylene ethers (that may comprise from 1 to 150 oxyethylene and/or oxypropylene groups) of fatty alcohols (particularly C8-C24 and preferably C12-C18 alcohols) such as oxyethylene ether of cetearylic alcohol with 30 oxyethylene groups (CTFA name "Ceteareth-30"), oxyethylene ether of stearylic alcohol with 20 oxyethylene groups (CTFA name "Steareth-20"), and oxyethylene ether of the mix of C12-C15 fatty alcohols containing 7 oxyethylene groups (CTFA name "C12-15 Pareth-7") marketed under the name NEODOL 25-7® by SHELL CHEMICALS, fatty acid esters (in particular C8-C24 acid, and preferably C16-C22) and polyethylene glycol (able to comprise from 1 to 150 ethyleneglycol patterns) such as PEG-50 stearate and PEG-40 monostearate sold under the trade name MYRJ 52P® by ICI UNIQUEMA, fatty acid esters (particularly C8-C24 acid, and preferably C16-C22 acid) and oxyethylenated and/or oxypropylated glycerol ethers (that may include 1 to 150 oxyethylanated and/or oxypropylenated groups), such as PEG-200 glyceryl monostearate sold particularly under the name Simulsol 220 TM® by SEPPIC; polyethoxylated glyceryl stearate with 30 ethylene oxide groups such as the TAGAT S® product sold by GOLDSCHMIDT, polyethoxylated glyceryl oleate with 30 ethylene oxide groups like the TAGAT O® product sold by GOLDSCHMIDT, polyethoxylated glyceryl cocoate with 30 ethylene oxide groups like the VARIONIC LI 13® product sold by SHEREX, polyethoxylated glyceryl isostearate with 30 ethylene oxide groups such as the TAGAT L® product sold by GOLDSCHMIDT and polyethoxylated glyceryl laurate with 30 groups of ethylene oxide like the TAGAT I® product from GOLDSCHMIDT, fatty acid esters (particularly C8-C24 acid and preferably C16-C22 acid) and oxyethylenated and/or oxypropylenated sorbitol ethers (possibly containing 1 to 150 oxyethylenated and/or oxypropylenated groups), such as polysorbate 20 sold under the name Tween 20® by CRODA, polysorbate 60 sold under the name Tween 60® by CRODA, polydimethylsiloxanes comprise both oxyethylenated groups and oxypropylene groups, such as dimethicone copolyol with INCI name PEG/PPG-17/18 DIMETHICONE, such as that sold under the trade name Q2-5220 Resin Modifier® by DOW CORNING, dimethicone copolyol benzoate (FINSOLV SLB 101® and 201® from FINTEX), copolymers of propylene oxide and of ethylene oxide (also called EO/PO polycondensates), and more particularly copolymers consisting of polyethylene glycol/polypropylene glycol blocks, such as for example polyethylene glycol/polypropylene glycol/polyethylene glycol triblock polycondensates, for example those having the following chemical structure:

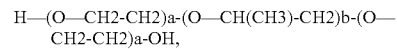

in which formula a ranges from 2 to 120, and b ranges from 1 to 100.

As a EO/PO polycondensate that can be used, mention can be made of polyethylene glycol/polypropylene glycol/polyethylene glycol triblock polycondensates sold under the trade names SYNPERONIC® such as SYNPERONIC PE/L44® and SYNPERONIC PE/F127® by ICI;

d) cationic surfactants such as primary, secondary or tertiary fatty amine salts, optionally polyoxyalkylene, quaternary ammonium salts, and mixtures thereof. As quaternary ammonium salts, mention can in particular be made of those satisfying the following general formula:

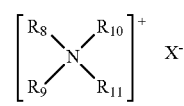

wherein:

R8 to R11, identical or different, each represent an aliphatic group, linear or branched, comprising from 1 to 30 carbon atoms, or an aromatic group such as aryl or alkylaryl, with the understanding that at least one of the R8 to R11 groups comprise from 8 to 30 carbon atoms, and preferably from12 to 24 carbon atoms. Preferably, the R8 to R11 aliphatic groups are chosen from C1-C30 alkyl groups, C1-C30 alkoxy, polyoxyalkylene (C2-C6), C1-C30 alkylamide, alkyl(C12-C22)amidoalkyl (C2-C6), alkyl(C12-C22)acetate, and C1-C30 hydroxyalkyl; and X— is an organic or inorganic anionic counter ion, such as the one chosen from halides, acetates, phosphates, nitrates, alkyl(C1-C4)sulfates, alkyl(C1-C4)- or alkyl (C1-C4)aryl-sulfonates, in particular methylsulfate and ethylsulfate.

Among the quaternary ammonium salts, preference is given to tetradecyltrimethylammonium, cetyltrimethylammonium, behenyltrimethylammonium, dipalmitoylethyl-hydroxyethylmethylammonium salts, and more particularly tetradecyltrimethylammonium bromide, behenyltrimethylammonium chloride, cetyltrimethylammonium chloride or dipalmitoylethylhydroxyethylammonium methosulfate; and e) mixtures thereof.

According to an embodiment, the surfactant is present in the composition according to the invention in a content ranging from 0.1% to 10% by weight, preferably from 1% to 5% by weight in relation to the total weight of the composition.

Preferably the surfactant is chosen from non-ionic surfactants with a HLB greater than or equal to 8 at 25° C., such as those mentioned hereinabove (group c). Such a surfactant contributes indeed in particular to the formation of micelles within the composition. These micelles can be detected by physico-chemical methods, such as the DRX optical method.

The composition can also comprise ingredients that are commonly used in cosmetics such as antioxidants, preservatives, perfumes, neutralizers, vitamins or mixtures thereof.

Obviously, those skilled in the art will take care to choose these optional additional compounds, and/or the quantity thereof, such that the advantageous properties of the active constituents of the composition according to the invention are not, or are substantially not, altered by the envisaged addition.

This invention also relates to the use of the compositions such as defined hereinabove for the demake-up and/or the cleaning of keratin materials, preferably of the skin and/or of keratin fibers (such as the eyelashes), in particular covered by a composition of coating keratin materials.

The term "composition of coating keratin materials" preferably means a makeup composition, such as a mascara or a foundation.

Such a composition in particular comprises at least 15% by weight of wax(es) (the wax being such as described hereinabove) in relation to the total weight of the composition, and/or at least 30% by weight of oil(s) (the oil being as described hereinabove) in relation to the total weight of the composition.

This invention also has for purpose a method of makeup removal and/or cleaning of keratin materials, preferably the skin and/or keratin fibers, in particular eyelashes, comprising the application on the keratin materials of a composition according to the invention.

The present invention also has for object a kit comprising:
on the one hand, a composition of coating keratin materials, in particular such as described hereinabove, and
on the other hand, a composition according to the invention.

The kit can in particular constitute a cosmetic assembly. The kit according to the invention contains in particular a composition of coating keratin materials and the composition according to the invention, under the same blister.

Throughout the application, the term "comprising a" or "including a" means "comprising at least one" or "including at least one", unless otherwise specified.

The invention is now illustrated by the following non-limiting examples. The percentages are expressed by weight in relation to the total weight of the composition (% w/w), unless mentioned otherwise.

EXAMPLE 1

Micellar Milk According to the Invention

| Ingredient | Quantity (% w/w) |
|---|---|
| Preservatives | Qs |
| Glycols | 7 |
| Betaine (trimethylglycine) (GENENCARE OSMS BA, DANISCO) | 1 |
| Sodium polyacrylate (Cosmedia SP)** | 0.3 |
| Xanthan gum | 0.09 |
| Monolaurate of sorbitan oxyethylene (20 OE) (polysorbate-20) (TWEEN 20-LQ-(CQ), CRODA) | 2 |
| Isopropyl myristate | 1.5 |
| Perfume | Qs |
| Cross-linked methacrylic acid/ethyl acrylate copolymer (CARBOPOL AQUA SF-1 from NOVEON)* | 1 |
| Plant extract | 0.1 |
| Citric acid | Qs pH |
| Water | Qsp100 |

*or 0.3% by weight of active material
**or 0.27% by weight of active material

The micellar milk is prepared as follows:

A portion of the water is mixed with the glycols, the betaine and the preservatives, at a temperature of about 68° C.

Then, to the preceding mixture is added sodium polyacrylate and xanthan gum before the temperature of the composition reaches 60° C. This is homogenized.

Afterwards, stopping the heating, the polysorbate-20 is added and this is homogenized. Then the isopropyl myristate and the perfume (fatty phase) are added, then this is homogenized at ambient temperature.

Afterwards, the adding of the cross-linked methacrylic acid/ethyl acrylate copolymer has to be done at a pH in the vicinity of 6.0. The whole is homogenized by adding the remaining water.

Finally, at ambient temperature, the plant extract is added then the citric acid in order to obtain a final pH of 6.2.

In the end, a smooth and shiny white homogeneous fluid is obtained.

EXAMPLE 2

Comparison of the Formula According to Example 1 with a Comparative Formula Comprising a Carrageenan The formula of the aforementioned example 1 is evaluated for its stability in centrifugation at 2200 rpm, for 1 hour or 10 days at 55° C., or 2 months at 45° C., or 36 months at ambient temperature.

It is stable in all of these conditions.

It is compared with the following comparative formula. This comparative formula does not contain any polysaccharide gelling agent comprising at least one glucose monomer:

| Ingredient | Quantity (% w/w) |
|---|---|
| Glycols | 7 |
| Preservatives | Qs |
| Betaine (trimethylglycine) (GENENCARE OSMS BA, DANISCO) | 1 |

-continued

| Ingredient | Quantity (% w/w) |
|---|---|
| Provitamin B5 | 0.01 |
| Sodium polyacrylate (Cosmedia SP)** | 0.3 |
| Carrageenan gum | 0.16 |
| Monolaurate of sorbitan oxyethylene (20 OE) (polysorbate-20) (TWEEN 20-LQ-(CQ), CRODA) | 1 |
| DISODIUM COCOYL GLUTAMATE (and) SODIUM COCOYL GLUTAMATE (AMISOFT CS 22/AJINOMOTO) | 1 |
| Isopropyl myristate | 1.5 |
| Cross-linked methacrylic acid/ethyl acrylate copolymer (CARBOPOL AQUA SF-1 from NOVEON)* | 1.2 |
| Citric acid | Qs |
| Water | Qsp100 |

*or 0.36% by weight of active material
**or 0.27% by weight of active material

These tests show that only the formula of the example 1 according to the invention is stable.

EXAMPLE 3

Comparison of the Formula According to Example 1 with Comparative Formulae

The formula of the aforementioned example 1 is evaluated for its stability in centrifugation after 24 h at ambient temperature. It is stable in this condition, and its viscosity (measured as described above) is less than 250 Cps.

Formula of example 1 is compared with the same formula, but which does not comprise any cross-linked methacrylic acid/ethyl acrylate copolymer (CARBOPOL AQUA SF-1 from NOVEON). Thus, the 1% of this commercial ingredient (corresponding to 0.3% by weight of active material) are replaced by water, to give comparative formula FC1. The same process for making the formula as in example 1 is used. FC1 shows a viscosity of less than 250 Cps, but after centrifugation, FC1 is totally unstable, as a complete separation of the phases is observed.

Formula of example 1 is also compared with the same formula, but in which the 1% of CARBOPOL AQUA SF-1 corresponding to 0.3% by weight of active material, are replaced by 0.3% of Pemulen TR-1 Polymer from Lubrizol (Acrylates/C10-30 Alkyl Acrylate Crosspolymer; 100% by weight of active material), to give comparative formula FC2. The same process for making the formula as in example 1 is used.

FC2 is stable, but shows a viscosity of around 2100 Cps.

Thus, these tests show that only the formula of the invention is fluid and stable.

The invention claimed is:

1. A composition comprising:
    an oily phase dispersed in an aqueous phase,
    at least one homopolymer of non-superabsorbent acrylic acid that is at least partially neutralized,
    at least one cross-linked copolymer of (meth)acrylic acid and of C1-C6 alkyl acrylate,
    at least one polysaccharide gelling agent comprising at least one glucose monomer, and said composition having a pH greater than or equal to 5.5 and less than 7, and which has a viscosity less than 250 Cps.

2. The composition according to claim 1, wherein the oily phase of the composition represents a percentage ranging from 0.1% to 10% with respect to the total weight of the composition.

3. The composition according to claim 1, wherein the at least partially neutralized non-superabsorbent acrylic acid homopolymer is chosen from among sodium polyacrylates and potassium polyacrylates.

4. The composition according to claim 1, wherein the homopolymer of non-superabsorbent acrylic acid is present in a content of active material ranging from 0.01% to 6% by weight with respect to the total weight of the composition.

5. The composition according to claim 1, wherein the cross-linked copolymer of (meth)acrylic acid and of C1-C6 alkyl acrylate comprises a monomer of C1-C6 alkyl acrylate chosen from methyl acrylate, ethyl acrylate, n-butyl acrylate, 2-hydroxyethyl acrylate, styrene, acrylamide, N,N-dimethylacrylamide, tertio-butylacrylamide, methyl methacrylate, ethyl methacrylate, n-butyl methacrylate and 2-hydroxyethyl methacrylate.

6. The composition according to claim 1, wherein the cross-linked copolymer of (meth)acrylic acid and of C1-C6 alkyl acrylate is chosen from a cross-linked copolymer of methacrylic acid and C1-C6 alkyl acrylate, a cross-linked copolymer of acrylic acid and C1-C6 alkyl acrylate.

7. The composition according to claim 1, wherein the cross-linked copolymer of (meth)acrylic acid and C1-C6 alkyl acrylate is present in a concentration of active material ranging from 0.01% to 0.6% by weight, preferably from 0.1% to 0.5% by weight, and more particularly from 0.2% to 0.4% by weight with respect to the total weight of the composition.

8. The composition according to claim 1, wherein the polysaccharide gelling agent comprising at least one glucose monomer is chosen from homo- and heteropolysaccharides comprising at least one glucose monomer.

9. The composition according to claim 1, wherein the polysaccharide gelling agent comprising at least one glucose monomer is present in a content of active material ranging from 0.01% to 0.5% by weight with respect to the total weight of the composition.

10. The composition according to claim 1, which has a pH greater than or equal to 5.9.

11. The composition according to claim 1, wherein the aqueous phase comprises water and optionally an organic solvent soluble in water, chosen from among linear or branched alkanols with 2 to 4 carbon atoms; polyols with 2 to 20 carbon atoms, and mixtures thereof.

12. The composition according to claim 1, which comprises from 50 to 98% by weight of water relative to the total weight of the composition, and/or which comprises 0.01 to 15% by weight of organic solvent(s) relative to the total weight of the composition.

13. A kit comprising:
    on the one hand a composition of coating keratin materials, and
    on the other hand a composition according to claim 1.

14. The composition according to claim 3, wherein the oily phase of the composition represents a percentage ranging from 0.1% to 10%.

15. The composition according to claim 4, wherein the at least partially neutralized non-superabsorbent acrylic acid homopolymer is chosen from among sodium polyacrylates and potassium polyacrylates.

16. The composition according to claim 2, wherein the at least partially neutralized non-superabsorbent acrylic acid homopolymer is chosen from among sodium polyacrylates and potassium polyacrylates.

17. The composition according to claim 2, wherein the homopolymer of non-superabsorbent acrylic acid is present in a content of active material ranging from 0.01% to 0.6% by weight.

18. The composition according to claim 1, which has a pH between 6.0 and 6.5.

\* \* \* \* \*